(12) United States Patent
Thomas et al.

(10) Patent No.: US 11,308,056 B2
(45) Date of Patent: *Apr. 19, 2022

(54) SYSTEMS AND METHODS FOR SNP ANALYSIS AND GENOME SEQUENCING

(71) Applicant: NOBLIS, INC., Reston, VA (US)

(72) Inventors: Sterling Thomas, Woodbridge, VA (US); Nathan Dellinger, Aldie, VA (US)

(73) Assignee: NOBLIS, INC., Reston, VA (US)

( * ) Notice: Subject to any disclaimer, the term of this patent is extended or adjusted under 35 U.S.C. 154(b) by 330 days.

This patent is subject to a terminal disclaimer.

(21) Appl. No.: 16/257,552

(22) Filed: Jan. 25, 2019

(65) Prior Publication Data

US 2019/0146962 A1 May 16, 2019

Related U.S. Application Data

(63) Continuation of application No. 13/904,738, filed on May 29, 2013, now Pat. No. 10,191,929.

(51) Int. Cl.
*G06F 16/00* (2019.01)
*G06F 16/22* (2019.01)
(Continued)

(52) U.S. Cl.
CPC ......... *G06F 16/2255* (2019.01); *G16B 30/00* (2019.02); *G16B 30/10* (2019.02)

(58) Field of Classification Search
CPC .............................. G06F 16/2255; G16B 30/00
See application file for complete search history.

(56) References Cited

U.S. PATENT DOCUMENTS

| | | |
|---|---|---|
| 5,994,068 A | 11/1999 | Guilfoyle et al. |
| 6,141,657 A | 10/2000 | Rothberg et al. |

(Continued)

FOREIGN PATENT DOCUMENTS

| | | |
|---|---|---|
| CA | 2036946 | 10/2001 |
| CN | 102682226 | 9/2012 |

(Continued)

OTHER PUBLICATIONS

Flicek et al. (Nov. 2009). "Sense from Sequence Reads: Methods for Alignment and Assembly," Nature Methods Supplement 6(11): 6-12; Corrigendum: 1.

(Continued)

*Primary Examiner* — Augustine K. Obisesan
(74) *Attorney, Agent, or Firm* — Morrison & Foerster LLP

(57) ABSTRACT

In some embodiments, techniques for identifying one or more species in an undifferentiated environmental sample comprising a plurality of nucleic acid sequences are provided. One or more indices that represent a plurality of reference nucleic acid sequences may be provided, and data may be received comprising digital representations of respective nucleic acid sequences. The respective nucleic acid sequences may be aligned, if possible, using the indices. A respective alignment ration may be calculated for each one of the reference nucleic acid sequences, based on the number of nucleic acid sequences aligned to the respective reference nucleic acid sequence and the total number of nucleic acid sequences in the received data.

13 Claims, 6 Drawing Sheets

Specification includes a Sequence Listing.

(51) Int. Cl.
  *G16B 30/00* (2019.01)
  *G16B 30/10* (2019.01)

(56) References Cited

U.S. PATENT DOCUMENTS

| | | | |
|---|---|---|---|
| 6,280,948 B1 | 8/2001 | Guilfoyle et al. | |
| 6,344,316 B1* | 2/2002 | Lockhart | G16B 25/20 |
| | | | 506/9 |
| 6,571,199 B1* | 5/2003 | Floratos | G06K 9/6255 |
| | | | 702/179 |
| 8,209,130 B1 | 6/2012 | Kennedy et al. | |
| 8,812,243 B2 | 8/2014 | Cardonha et al. | |
| 2002/0058256 A1 | 5/2002 | Rothberg et al. | |
| 2002/0102610 A1* | 8/2002 | Townsend | G01N 33/6848 |
| | | | 435/7.1 |
| 2004/0002816 A1 | 1/2004 | Milosavljevic | |
| 2004/0048264 A1 | 3/2004 | Stoughton et al. | |
| 2004/0053246 A1 | 3/2004 | Sorenson | |
| 2004/0224330 A1 | 11/2004 | He | |
| 2005/0049795 A1* | 3/2005 | Fikuda | G16B 30/00 |
| | | | 702/20 |
| 2005/0107960 A1* | 5/2005 | Toyoda | G16B 50/00 |
| | | | 702/19 |
| 2005/0239102 A1* | 10/2005 | Verdine | C12Q 1/6811 |
| | | | 435/6.12 |
| 2006/0112264 A1 | 5/2006 | Agarwal | |
| 2006/0286566 A1 | 12/2006 | Lapidus et al. | |
| 2007/0016612 A1 | 1/2007 | James et al. | |
| 2008/0027656 A1* | 1/2008 | Parida | G16B 10/00 |
| | | | 702/20 |
| 2008/0168572 A1 | 7/2008 | Stetter et al. | |
| 2009/0055425 A1 | 2/2009 | Evans et al. | |
| 2009/0233802 A1 | 9/2009 | Bignell et al. | |
| 2009/0270277 A1 | 10/2009 | Glick et al. | |
| 2009/0292665 A1 | 11/2009 | Den Hartog | |
| 2010/0114918 A1* | 5/2010 | Karlsen | G16B 30/00 |
| | | | 707/754 |
| 2010/0287165 A1 | 11/2010 | Halpern et al. | |
| 2011/0103501 A1 | 5/2011 | Khojastepour et al. | |
| 2011/0257889 A1 | 10/2011 | Klammer et al. | |
| 2011/0264377 A1 | 10/2011 | Cleary | |
| 2011/0270533 A1* | 11/2011 | Zhang | G16B 30/00 |
| | | | 702/20 |
| 2011/0295858 A1 | 12/2011 | Ahn et al. | |
| 2012/0016666 A1 | 1/2012 | Wu et al. | |
| 2012/0046877 A1* | 2/2012 | Hyland | C12Q 1/6809 |
| | | | 702/20 |
| 2012/0296810 A1* | 11/2012 | Bates | G06Q 50/28 |
| | | | 705/39 |
| 2013/0053541 A1* | 2/2013 | Shankar | G01N 33/6845 |
| | | | 530/300 |
| 2013/0090266 A1* | 4/2013 | Gardner | G16B 15/30 |
| | | | 506/24 |
| 2013/0203973 A1* | 8/2013 | Wilkerson | C08H 6/00 |
| | | | 530/505 |
| 2013/0268206 A1 | 10/2013 | Porreca et al. | |
| 2013/0304392 A1* | 11/2013 | Deciu | G16B 20/20 |
| | | | 702/20 |
| 2013/0338934 A1 | 12/2013 | Asadi et al. | |
| 2014/0075183 A1 | 3/2014 | Wang et al. | |
| 2014/0235456 A1* | 8/2014 | Garner, Jr | G16B 35/00 |
| | | | 506/2 |
| 2014/0358937 A1 | 12/2014 | Thomas et al. | |
| 2016/0306919 A1 | 10/2016 | Ding et al. | |
| 2016/0344849 A1 | 11/2016 | Thomas et al. | |
| 2018/0330053 A1 | 11/2018 | Ivancich et al. | |

FOREIGN PATENT DOCUMENTS

| | | |
|---|---|---|
| WO | 94/01582 | 1/1994 |
| WO | 01/098535 A2 | 12/2001 |
| WO | 2005/096208 A1 | 10/2005 |
| WO | 2007/137225 A2 | 11/2007 |
| WO | 2008/000090 A1 | 1/2008 |
| WO | 2010/104608 A2 | 9/2010 |
| WO | 2012/168815 A2 | 12/2012 |

OTHER PUBLICATIONS

Hancock-Hanser et al. (2013). "Targeted Multiplex Next-Generation Sequencing: Advances in Techniques of Mitochondrial and Nuclear DNA Sequencing for Population Genomics," Molecular Ecology Resources 13: 254-268.

International Search Report and Written Opinion dated Sep. 7, 2016, directed to International Application No. PCT/US2016/033786; 9 pages.

Li et al. (Jun. 1, 2009). "SNP Detection for Massively Parallel Whole-Genome Resequencing," Genome Research 19: 1124-1132.

Mehta et al. (2010). "DNA Compression Using Hash Based Data Structure," International Journal of Information Technology and Knowledge Management 2(2): 383-386.

Munoz-Torres et al. (2011). "Hymenoptera Genome Database: Integrated Community Resources for Insect Species of The Order Hymenoptera," Nucleic Acids Research 39(1): D658-D662.

Ning et al. (2011). "SSAHA: A Fast Search Method for Large DNA Databases," Genome Research 11: 1725-1729.

Office Action dated Oct. 19, 2017, directed to Chinese Application No. 201410228956.7; 10 pages.

Ossowski et al. (Oct. 3, 2008). "Sequencing of Natural Strains of *Arabidopsis thaliana* with Short Reads," Genome Research 18: 2024-2033.

Search Report dated May 7, 2015, directed to European Application No. 14170198.7, 17 pages.

Thomas et al., U.S. Office Action dated Nov. 27, 2017, directed to U.S. Appl. No. 14/718,950; 19 pages.

Thomas et al., U.S. Office Action dated Dec. 29, 2016, directed to U.S. Appl. No. 13/904,738; 23 pages.

Thomas et al., U.S. Office Action dated Jan. 28, 2015, directed to U.S. Appl. No. 13/904,738; 17 pages.

Thomas et al., U.S. Office Action dated Jun. 27, 2018, directed to U.S. Appl. No. 13/904,738; 32 pages.

Thomas et al., U.S. Office Action dated Mar. 24, 2016, directed to U.S. Appl. No. 13/904,738; 21 pages.

Thomas et al., U.S. Office Action dated May 24, 2017, directed to U.S. Appl. No. 14/718,950; 14 pages.

Thomas et al., U.S. Office Action dated May 28, 2015, directed to U.S. Appl. No. 13/904,738; 22 pages.

Thomas et al., U.S. Office Action dated Nov. 1, 2017, directed to U.S. Appl. No. 13/904,738; 24 pages.

Thomas et al., U.S. Office Action dated May 30, 2018, directed to U.S. Appl. No. 14/718,950; 21 pages.

Tsaftaris et al. (2007). "Retrieval Accuracy of Very Large DNA-Based Databases of Digital Signals," European Signal Processing Conference (EUSIPCO): 1561-1565.

Thomas et al., Office Action dated Feb. 13, 2019, directed to U.S. Appl. No. 14/718,950; 12 pages.

Examination Report dated Dec. 12, 2019, directed to IN Application No. 1682/MUM/2014; 7 pages.

\* cited by examiner

200

206
...GTAAGATCCGCTACAA...ATCCGCTAATGCGCCGTAGTCCG...

202a

| 0 | AAAAAAAAAAAAAAAA |
| 1 | AAAAAAAAAAAAAAAT |
| 2 | AAAAAAAAAAAAAATA |
| 3 | AAAAAAAAAAAAAATT |

202b

| $n$ | GTAAGATCCGCTACAA | → | 0 | → | 21 |
| $n+1$ | GTAAGATCCGCTACAT | | | | |
| $n+2$ | GTAAGATCCGCTACTA | → | 44 | | |

204a  204b 202c  204c

| $4^k$-4 | CGCCCCCCCCCCCCCG |
| $4^k$-3 | CGCCCCCCCCCCCCGC |
| $4^k$-2 | CGCCCCCCCCCCCCCC |
| $4^k$-1 | CCCCCCCCCCCCCCCC |

SEQUENCE LISTING

<160> NUMBER OF SEQ ID NOS: 14

<210> SEQ ID NO 1
<211> LENGTH: 16
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 1
attgcttcca tgggtc                                                         16

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ser Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Leu Ala Thr Tyr Phe Cys Leu Gln His Ser Tyr Leu Pro Tyr
                85                  90                  95

Thr Phe Gly Gly Gly Thr Lys Leu Glu Ile Lys Arg
            100                 105

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa aaaaaa                                                         16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaaa aaaatt                                                         16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtaagatccg ctacaa                                                         16
```

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 6
gtaagatccg ctacta                                                   16

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 7
atccgctaat gcgccgtagt ccg                                           23

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 8
aaaaaaaaaa aaaaat                                                   16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 9
aaaaaaaaaa aaaata                                                   16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 10
gtaagatccg ctacat                                                   16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 11
cgcccccccc ccccg                                                    16

```
<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgcccccccc ccccgc                                                     16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgcccccccc cccccc                                                     16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cccccccccc cccccc                                                     16
```

SYSTEMS AND METHODS FOR SNP ANALYSIS AND GENOME SEQUENCING

CROSS-REFERENCE TO RELATED APPLICATIONS

This application is a continuation of U.S. patent application Ser. No. 13/904,738, filed May 29, 2013, the entire contents of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739642002201 SEQLIST.TXT, date recorded: Jan. 25, 2019, size: 5 KB).

FIELD OF THE INVENTION

Embodiments disclosed herein relate generally to creating and using application-specific indices on computer systems, and more particularly, to systems and methods for creating an index of nucleic acid sequences or amino acid sequences based on a received sample.

BACKGROUND OF THE INVENTION

A single-nucleotide polymorphism, or SNP, is a single nucleotide differences between DNA sequences from individuals of the same species or between the paired chromosomes in an individual. For example, a segment of DNA may include the nucleotide sequence TTTCTTGTA in one individual (or on the first paired chromosome), and the corresponding segment of DNA may include the nucleotide sequence TTCCTTGTA in another individual (or on the second paired chromosome). Each of these different sequences are called alleles.

Many SNPs are not harmful. Most SNPs are found between genes (e.g., in the exons) or in the non-coding regions of genes. These non-coding SNPs are useful in DNA fingerprinting technologies.

Even when SNPs occur in the coding regions of genes, the SNP may be synonymous with a wild type gene, and thus the SNP may not affect the amino acid sequence ultimately transcribed. For example, TTT and TTC will both be transcribed as the amino acid phenylalanine.

The genetic variation provided by coding-region SNPs leads to the normal variation in phenotype in a given species. The alleles are what give people different genetic traits, such as blonde, brunette, red, or black hair, for example. Some coding-region SNPs, however, can cause genetically linked diseases or disorders. Because some illnesses can be traced back to SNPs, geneticists have been interested in mapping and detecting SNPs.

A mutation in one gene is enough to cause some diseases such as Huntington's disease and polysystic kidney disease 1 and 2. More often, however, multiple SNPs are involved in causing complex disorders like asthma, cancers, diabetes, heart disease, and many others. In these complex disorders, the existence of one or more SNPs may act as an indicator that a person is at a higher risk of developing the disorder. SNPs are also associated with the metabolism of drugs, giving rise to the possibility of individualized medicine where treatment is provided to an individual depending upon his or her genetic make-up.

SNPs are detected in a number of ways. For example, one method uses SNP chips, which are small silicon glass wafers with single-stranded DNA fragments attached. Each attached single-stranded DNA fragment has a unique sequence that corresponds to a known SNP. A sample of the DNA is converted into single-stranded DNA, and a fluorescent dye label is added. The labeled sample DNA fragments are incubated on the chip, and the labeled sample DNA with a nucleotide sequence matching a known SNPs would hybridize to the known SNP bound on the chip. The DNA that did not bind is washed away, and then a computer scans the chip to detect the location of the fluorescent labels, thereby detecting sample DNA bound to the DNA with known SNPs and, thus, identifying the SNPs in the DNA sample. This procedure is time consuming, however, and only known SNPs are detected.

Related to the detection of SNPs is the sequencing of DNA. In order to develop the set of known SNPs, one must first sequence DNA to act as the reference for unknown samples. SNP chips are a viable method for identifying SNPs because the human genome (and other genomes) have been sequenced in their entirety. By comparing several genomes within the same species and/or the same gene from several genomes, consensus sequences are created, and variations from the consensus sequences are identified as SNPs.

Shotgun sequencing is a commonly used method for sequencing entire genomes. In shotgun sequencing, DNA is fragmented into random segments. These segments are sequenced, and the determined sequences of nucleic acid fragments are called "reads." The fragmenting process generates overlapping reads, which are aligned based on their overlapping regions.

Even though sequence alignments are done by computer, sequencing is still a time-consuming process. Bowtie, a software program for aligning sequences, claims to be able to align 25 million 35 base pairs reads each per hour. Bowtie also creates an index for a genome using a Burrows-Wheeler index. Thus, using the Bowtie program to build an index for a human genome, which includes approximately 3 billion base pairs, would take over 8 hours. Furthermore, detecting known human SNPs using the SNP chip method may require hours to prepare and process the chips, as described above, and novel SNPs cannot be detected with SNP chips.

Related to the field of sequencing DNA is the study of metagenomics. Metagenomics is the study of the myriad of genomes obtained directly from the environment, which is especially important in the study of microorganisms that cannot be cultured or easily studied in the lab. Metagenomics is used to understand the genetic diversity in an environment. In metagenomics, all of the genetic material of an environmental sample may be studied as a whole without first separating and identifying the genetic material with a particular species. One aspect of metagenomics research, however, is focused on determining which species are present in undifferentiated samples by sequencing DNA in the sample and comparing it to known DNA sequences. DNA sequencing in metagenomics is also used to discover previously unknown species when the sequencing reveals a novel genome. Often, the novel genome can be categorized by genus, even if the species has never been identified before.

Metagenomics also involves developing a way to determine whether a particular species is in a sample containing DNA from several species. One method of determining the species in a sample may involve sequencing the genetic material from a sample and then comparing the sequences to libraries of known sequences to determine what species are present. Often, the sequences are not resolved into entire genomes before comparing them to known sequences. Instead, the sequence "reads" are compared to sequence libraries to determine the percentage of sample sequences that match species' sequences in the library. The higher the percentage match for a certain species, the more likely that DNA from species is present in the sample. Given the current sequence analysis technologies, this is a time-intensive task.

In light of the above, there is a need for faster methods of analyzing sequence DNA and detecting SNPs. There is also a need for faster ways to sequence and identify multiple genomes from environmental samples and detect the presence of a single genome in samples containing many genomes. Finally, there exists a need for the simultaneous sequencing and comparing of the sequence, such that SNPs can be identified before the entire genome is sequenced so a genome or sequence can be identified before the sequencing is complete.

SUMMARY OF THE INVENTION

Disclosed embodiments include systems and methods for sequencing nucleic acid sequences, including DNA, RNA, and synthetic sequences, using an index. Systems and methods for identifying SNPs within a sequence and for identifying a sequence, for example, by genus or species, during or after the sequence determination, using an index, are also disclosed. Disclosed embodiments include systems and methods for sequencing peptides and proteins, including sequences incorporating standard and nonstandard amino acids, using an index. Systems and methods for identifying amino acid substitutions within a sequence, during or after the sequence determination, using an index, are also disclosed.

A method for creating an index for a nucleic acid sequence is provided. The method generates the index. The index comprises a plurality of elements and each element corresponds to a permutation of the nucleic acid sequence. The method receives data representing the nucleic acid sequence and identifies, in the data, a subsequence of the nucleic acid sequence. The subsequence is retrieved from a first position of the nucleic acid sequence. The method computes a hash of the subsequence to determine a corresponding element of the index and stores, in the corresponding element of the index, position data reflecting the first position.

A method for aligning a nucleic acid sequence is provided. The method receives data representing the nucleic acid sequence and identifies, in the data, a subsequence of the nucleic acid sequence. The method computes a hash of the subsequence to determine a corresponding element of the index. The corresponding element includes position data reflecting one or more positions of a reference nucleic acid sequence containing a part of the subsequence. The method compares the subsequence with the reference nucleic acid sequence at the one or more positions of the reference nucleic acid sequence and, determines, based on the comparison, whether a number of bases greater than a predetermined threshold are mismatched. The method determines, when the number of mismatched bases is less than the predetermined threshold, that the subsequence is aligned with the reference nucleic acid sequence.

A method for detecting an SNP is provided. The method receives data representing a plurality of aligned nucleic acid sequences and generates, based on the plurality of aligned nucleic acid sequences, a consensus sequence. The method compares the consensus sequence with a reference nucleic acid sequence. The method determines, when an element of the consensus sequence and the corresponding element of the reference nucleic acid sequence are mismatched, and when a confidence level associated with the consensus sequence element exceeds a predetermined confidence threshold, that the element of the consensus sequence is an SNP.

A method for identifying one or more species in a sample of one or more nucleic acid sequences is provided. The method receives data representing a nucleic acid sequence and identifies, in the data, a plurality of subsequences of the nucleic acid sequence. The method aligns the plurality of subsequences to each of a plurality of indices. Each index represents at least one reference nucleic acid sequence. The method calculates, for each reference nucleic acid sequence, a ratio of the number of subsequences aligned to the reference nucleic acid sequence over the total number of subsequences, and, outputs the calculated ratios.

A method for creating an index for an amino acid sequence is provided. The method generates the index. The index comprises a plurality of elements and each element corresponds to a permutation of the amino acid sequence. The method receives data representing the amino acid sequence and identifies, in the data, a subsequence of the amino acid sequence. The subsequence is retrieved from a first position of the amino acid sequence. The method computes a hash of the subsequence to determine a corresponding element of the index and stores, in the corresponding element of the index, position data reflecting the first position.

A method for aligning an amino acid sequence is provided. The method receives data representing the amino acid sequence and identifies, in the data, a subsequence of the amino acid sequence. The method computes a hash of the subsequence to determine a corresponding element of the index. The corresponding element includes position data reflecting one or more positions of a reference amino acid sequence containing a part of the subsequence. The method compares the subsequence with the reference amino acid sequence at the one or more positions of the reference amino acid sequence and determines, based on the comparison, whether a number of amino acids greater than a predetermined threshold are mismatched. The method determines, when the number of mismatched amino acids is less than the predetermined threshold, that the subsequence is aligned with the reference amino acid sequence.

A method for detecting an amino acid substitution is provided. The method receives data representing a plurality of aligned amino acid sequences and generates, based on the plurality of aligned amino acid sequences, a consensus sequence. The method compares the consensus sequence with a reference amino acid sequence. The method determines, when an element of the consensus sequence and the corresponding element of the reference amino acid sequence are mismatched, and when a confidence level associated with the consensus sequence element exceeds a predetermined confidence threshold, that the element of the consensus sequence is an amino acid substitution.

A non-transitory computer-readable medium comprising program instructions, which, when executed by a processor, cause the processor to perform a method for creating an index for a nucleic acid sequence, is provided. The method generates the index. The index comprises a plurality of elements and each element corresponds to a permutation of the nucleic acid sequence. The method receives data representing the nucleic acid sequence and identifies, in the data, a subsequence of the nucleic acid sequence. The subsequence is retrieved from a first position of the nucleic acid sequence. The method computes a hash of the subsequence to determine a corresponding element of the index and stores, in the corresponding element of the index, position data reflecting the first position.

A non-transitory computer-readable medium comprising program instructions, which, when executed by a processor, cause the processor to perform a method for aligning a nucleic acid sequence, is provided. The method receives data representing the nucleic acid sequence and identifies, in the data, a subsequence of the nucleic acid sequence. The method computes a hash of the subsequence to determine a corresponding element of the index. The corresponding element includes position data reflecting one or more positions of a reference nucleic acid sequence containing a part of the subsequence. The method compares the subsequence with the reference nucleic acid sequence at the one or more positions of the reference nucleic acid sequence and determines, based on the comparison, whether a number of bases greater than a predetermined threshold are mismatched. The method determines, when the number of mismatched bases is less than the predetermined threshold, that the subsequence is aligned with the reference nucleic acid sequence.

A non-transitory computer-readable medium comprising program instructions, which, when executed by a processor, cause the processor to perform a method for detecting an SNP, is provided. The method receives data representing a plurality of aligned nucleic acid sequences and generates, based on the plurality of aligned nucleic acid sequences, a consensus sequence. The method compares the consensus sequence with a reference nucleic acid sequence. The method determines, when an element of the consensus sequence and the corresponding element of the reference nucleic acid sequence are mismatched, and when a confidence level associated with the consensus sequence element exceeds a predetermined confidence threshold, that the element of the consensus sequence is an SNP.

A non-transitory computer-readable medium comprising program instructions, which, when executed by a processor, cause the processor to perform a method for identifying one or more species in a sample of one or more nucleic acid sequences, is provided. The method receives data representing a nucleic acid sequence and identifies, in the data, a plurality of subsequences of the nucleic acid sequence. The method aligns the plurality of subsequences to each of a plurality of indices. Each index represents at least one reference nucleic acid sequence. The method calculates, for each reference nucleic acid sequence, a ratio of the number of subsequences aligned to the reference nucleic acid sequence over the total number of subsequences, and, outputs the calculated ratios.

A non-transitory computer-readable medium comprising program instructions, which, when executed by a processor, cause the processor to perform a method for creating an index for an amino acid sequence, is provided. The method generates the index. The index comprises a plurality of elements and each element corresponds to a permutation of the amino acid sequence. The method receives data representing the amino acid sequence and identifies, in the data, a subsequence of the amino acid sequence. The subsequence is retrieved from a first position of the amino acid sequence. The method computes a hash of the subsequence to determine a corresponding element of the index and stores, in the corresponding element of the index, position data reflecting the first position.

A non-transitory computer-readable medium comprising program instructions, which, when executed by a processor, cause the processor to perform a method for aligning an amino acid sequence, is provided. The method receives data representing the amino acid sequence and identifies, in the data, a subsequence of the amino acid sequence. The method computes a hash of the subsequence to determine a corresponding element of the index. The corresponding element includes position data reflecting one or more positions of a reference amino acid sequence containing a part of the subsequence. The method compares the subsequence with the reference amino acid sequence at the one or more positions of the reference amino acid sequence and determines, based on the comparison, whether a number of amino acids greater than a predetermined threshold are mismatched. The method determines, when the number of mismatched amino acids is less than the predetermined threshold, that the subsequence is aligned with the reference amino acid sequence.

A non-transitory computer-readable medium comprising program instructions, which, when executed by a processor, cause the processor to perform a method for detecting an amino acid substitution, is provided. The method receives data representing a plurality of aligned amino acid sequences and generates, based on the plurality of aligned amino acid sequences, a consensus sequence. The method compares the consensus sequence with a reference amino acid sequence. The method determines, when an element of the consensus sequence and the corresponding element of the reference amino acid sequence are mismatched, and when a confidence level associated with the consensus sequence element exceeds a predetermined confidence threshold, that the element of the consensus sequence is an amino acid substitution.

A system for creating an index for a nucleic acid sequence is provided. The system includes a processor and a memory storing instructions executable by the processor to generate the index. The index comprises a plurality of elements and each element corresponds to a permutation of the nucleic acid sequence. The instructions are further able to receive data representing the nucleic acid sequence and identify, in the data, a subsequence of the nucleic acid sequence. The subsequence is retrieved from a first position of the nucleic acid sequence. The instructions are further able to compute a hash of the subsequence to determine a corresponding element of the index, and store, in the corresponding element of the index, position data reflecting the first position.

A system for aligning a nucleic acid sequence is provided. The system includes a processor and a memory storing instructions executable by the processor to receive data representing the nucleic acid sequence. The instructions are further able to identify, in the data, a subsequence of the nucleic acid sequence, and compute a hash of the subsequence to determine a corresponding element of the index. The corresponding element includes position data reflecting one or more positions of a reference nucleic acid sequence containing a part of the subsequence. The instructions are further able to compare the subsequence with the reference nucleic acid sequence at the one or more positions of the reference nucleic acid sequence and determine, based on the comparison, whether a number of bases greater than a predetermined threshold are mismatched. The instructions are further able to determine, when the number of mismatched bases is less than the predetermined threshold, that the subsequence is aligned with the reference nucleic acid sequence.

A system for detecting an SNP is provided. The system includes a processor and a memory storing instructions executable by the processor to receive data representing a plurality of aligned nucleic acid sequences. The instructions are further able to generate, based on the plurality of aligned nucleic acid sequences, a consensus sequence. The instructions are further able to compare the consensus sequence with a reference nucleic acid sequence and, determine, when an element of the consensus sequence and the corresponding element of the reference nucleic acid sequence are mismatched, and when a confidence level associated with the consensus sequence element exceeds a predetermined confidence threshold, that the element of the consensus sequence is an SNP.

A system for identifying one or more species in a sample of one or more nucleic acid sequences is provided. The system includes a processor and a memory storing instructions executable by the processor to receive data representing a nucleic acid sequence. The instructions are further able to identify, in the data, a plurality of subsequences of the nucleic acid sequence and align the plurality of subsequences to each of a plurality of indices. Each index represents at least one reference nucleic acid sequence. The instructions are further able to calculate, for each reference nucleic acid sequence, a ratio of the number of subsequences aligned to the reference nucleic acid sequence over the total number of subsequences, and, output the calculated ratios.

A system for creating an index for an amino acid sequence is provided. The system includes a processor and a memory storing instructions executable by the processor to generate the index. The index comprises a plurality of elements and each element corresponds to a permutation of the amino acid sequence. The instructions are further able to receive data representing the amino acid sequence and identify, in the data, a subsequence of the amino acid sequence. The subsequence is retrieved from a first position of the amino acid sequence. The instructions are further able to compute a hash of the subsequence to determine a corresponding element of the index and, store, in the corresponding element of the index, position data reflecting the first position.

A system for aligning an amino acid sequence is provided. The system includes a processor and a memory storing instructions executable by the processor to receive data representing the amino acid sequence. The instructions are further able to identify, in the data, a subsequence of the amino acid sequence and compute a hash of the subsequence to determine a corresponding element of the index. The corresponding element includes position data reflecting one or more positions of a reference amino acid sequence containing a part of the subsequence. The instructions are further able to compare the subsequence with the reference amino acid sequence at the one or more positions of the reference amino acid sequence and determine, based on the comparison, whether a number of amino acids greater than a predetermined threshold are mismatched. The instructions are further able to determine, when the number of mismatched amino acids is less than the predetermined threshold, that the subsequence is aligned with the reference amino acid sequence.

A system for detecting an amino acid substitution is provided. The system includes a processor and a memory storing instructions executable by the processor to receive data representing a plurality of aligned amino acid sequences. The instructions are further able to generate, based on the plurality of aligned amino acid sequences, a consensus sequence and compare the consensus sequence with a reference amino acid sequence. The instructions are further able to determine, when an element of the consensus sequence and the corresponding element of the reference amino acid sequence are mismatched, and when a confidence level associated with the consensus sequence element exceeds a predetermined confidence threshold, that the element of the consensus sequence is an amino acid substitution.

It is to be understood that both the foregoing general description and the following detailed description are exemplary and explanatory only, and are not restrictive of the disclosed embodiments.

BRIEF DESCRIPTION OF THE DRAWINGS

The accompanying drawings, which are incorporated in and constitute a part of this specification, illustrate several embodiments. In the drawings:

FIG. 2 illustrates an example index of a nucleic acid sequence (SEQ ID NOS 5, 7, 3, 8-9, 4-5, 10, 6 and 11-2, respectively, in order of appearance), consistent with embodiments disclosed herein.

DETAILED DESCRIPTION OF THE INVENTION

Reference will now be made in detail to various embodiments, examples of which are illustrated in the accompanying drawings. Wherever possible, the same reference numbers will be used throughout the drawings to refer to the same or like parts. Moreover, use of the indefinite article "a" or "an" in the specification and the claims is meant to include one or more than one of the feature that it introduces, unless otherwise indicated.

Figure 1:
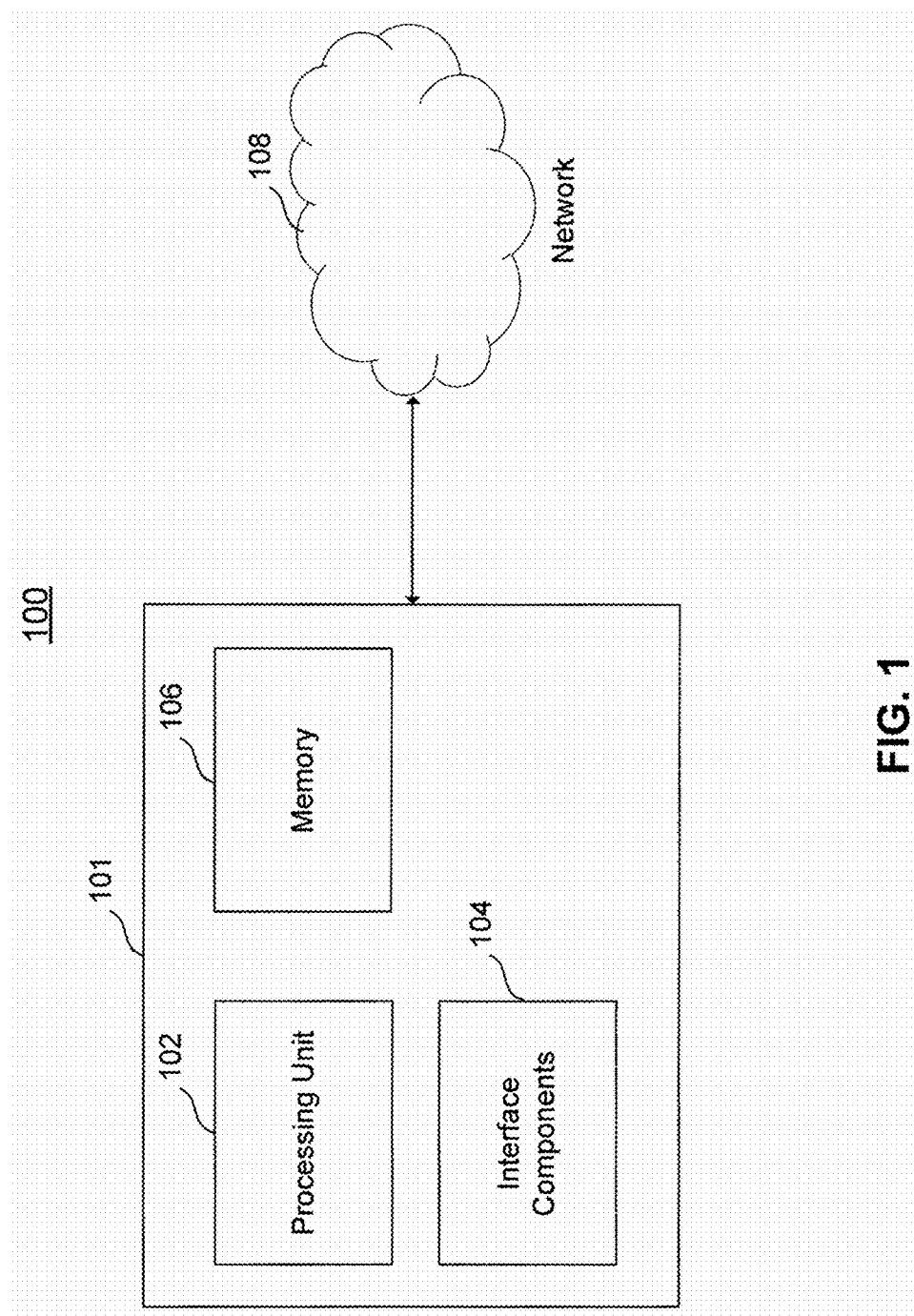
FIG. 1 is an example block diagram illustrating a computing system, consistent with embodiments disclosed herein.

FIG. 1 shows an exemplary system that is configured to perform one or more software processes that, when executed, provide one or more aspects of the disclosed embodiments. FIG. 1 is not intended to be limiting to the disclosed embodiment as the components used to implement the processes and features disclosed herein may vary.

In accordance with certain disclosed embodiments, a computing system 100 may be provided that includes a computer 101 and network 108. Other components known to one of ordinary skill in the art may be included in system 100 to process, transmit, provide, and receive information consistent with the disclosed embodiments.

Computer 101 may include computer system components, such as one or more servers, desktop computers, workstations, tablets, hand held computing devices, memory devices, and/or internal network(s) connecting the components. In one embodiment, computer 101 may be a server that includes one or more processors, memory devices, and interface components 104. For example, computer 101 may include processing unit 102, memory 106, and interface components 104. Computer 101 may be a single server or may be configured as a distributed computer system including multiple servers or computers that interoperate to perform one or more of the processes and functionalities associated with the disclosed embodiments.

Processing unit 102 may include one or more known processing devices, such as a microprocessor from the Pentium™ family manufactured by Intel™ or the Turion™ family manufactured by AMD™. Processing unit 102 may include a single core or multiple core processor system that provides the ability to perform parallel processes simultaneously. For example, processing unit 102 may include a single core processor that is configured with virtual processing technologies known to those skilled in the art. In certain embodiments, processing unit 102 may use logical processors to simultaneously execute and control multiple processes. The one or more processors in processing unit 102 may implement virtual machine technologies, or other similar known technologies to provide the ability to execute, control, run, manipulate, store, etc. multiple software processes, applications, programs, etc. In another embodiment, processing unit 102 may include a multiple-core processor arrangement (e.g., dual or quad core) that is configured to provide parallel processing functionalities to allow electronic computing system 100 to execute multiple processes simultaneously. One of ordinary skill in the art would understand that other types of processor arrangements, such as those used in Cray supercomputers, could be implemented that provide for the capabilities disclosed herein.

In some embodiments, computer 101 may be a supercomputer, such as the Cray XMT or Cray XMT 2. Supercomputers may include multiple-core processor arrangements paired with a memory that are configured to provide greater parallel processing functionalities relative to consumer-grade desktop computers, laptops, and the like. The Cray XMT, for example, may include 128 TB (terabytes) of memory and processor cores capable of executing up to 8,192 threads in parallel. Similarly, the Cray XMT 2 may include 512 TB of memory and 128 processor cores, with each processor core capable of executing 128 threads, for a total of 16,384 threads.

Computer 101 may include one or more storage devices configured to store information used by processing unit 102 (or other components) to perform certain functions related to the disclosed embodiments. In one example, memory 106 may include instructions to enable the one or more processors in processing unit 102 to execute one or more applications, such as server applications, network communication processes, and any other type of application or software known to be available on computer systems. Alternatively, the instructions, application programs, etc. may be stored in an external storage or available from a memory over network 108. The one or more storage devices may be a volatile or non-volatile, magnetic, semiconductor, tape, optical, removable, non-removable, or other type of storage device or tangible computer-readable medium.

In one embodiment, memory 106 may include instructions that, when executed by the one or more processors in processing unit 102, perform one or more processes consistent with the functionalities disclosed herein. Methods, systems, and articles of manufacture consistent with disclosed embodiments are not limited to separate programs or computers configured to perform dedicated tasks. For example, computer 101 may include a memory that may include one or more programs to perform one or more functions for creating an index of nucleic acid elemental sequences or amino acid elemental sequences of the disclosed embodiments. Moreover, the one or more processors in processing unit 102 may execute one or more programs located remotely from system 100. For example, system 100 may access one or more remote programs, that, when executed, perform functions related to disclosed embodiments. Memory 106 may include one or more memory devices that store data and instructions used to perform one or more features of the disclosed embodiments. Memory 106 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Computer 101 may also be communicatively connected to one or more memory devices (e.g., databases (not shown)) locally or through network 108. The remote memory devices may be configured to store information and may be accessed and/or managed by computer 101. By way of example, the remote memory devices may be document management systems, Microsoft SQL databases, SharePoint databases, Oracle™ databases, Sybase™ databases, or other relational databases. Systems and methods of disclosed embodiments, however, are not limited to separate databases or even to the use of a database.

Computer 101 may also include one or more I/O devices that may comprise one or more interfaces for receiving signals or input from input devices and providing signals or output to one or more output devices that allow data to be received and/or transmitted by electronic computing system 100. For example, interface components 104 may provide interfaces to one or more input devices, such as one or more keyboards, mouse devices, and the like, that enable computer 101 to receive data from one or more users. Further, interface components 104 may include components configured to send and receive information between components of computer 101 or external to computer 101, such as network 108.

Network 108 may be any type of network that provides communications, exchanges information, and/or facilitates the exchange of information between computer 101 and other users or computing systems. In one embodiment, network 108 may be the Internet, a Local Area Network, or other suitable connection(s) that enables computer 101 to send and receive information between the components of system 100.

Computer 101 may create an index of a nucleic acid sequence or an amino acid sequence. The index may include a plurality of elements, with each element corresponding to a permutation of a nucleic acid sequence or an amino acid sequence (or another type of sequence). Computer 101 may implement the index using a variety of data structures, such as databases, matrices, arrays, linked lists, trees, and the like. The choice of data structures may vary and is not critical to any embodiment. Computer 101 may store the index in memory 106. More specifically, the index may be stored on hard disk; computer 101 may also load the index into RAM for increased performance.

An example nucleic acid sequence is shown in Table 1, below.

TABLE 1

Example Nucleic Acid Sequence
12345678901234567890123456789012345678 90

ATTGCTTCCATGGGTC
(SEQ ID NO: 1)

As shown in Table 1, a nucleic acid sequence contains various combinations of the bases adenine, guanine, thymine, and cytosine, represented by the letters "A," "G," "T," and "C," respectively. The numerical digits included in Table 1 enable convenient identification of the positions of the different bases appearing in the sequence. For example, the base adenine appears in positions 1 and 10 of the sequence appearing in Table 1, which is 16 bases in length.

An example amino acid sequence is shown in Table 2, below.

TABLE 2

Example Amino Acid Sequence
12345678901234567890123456789012345678 90

DVQMIQSPSSLSASLGDIVTMTCQASQGTSINLNWFQQKP
GKAPKLLIYGSSNLEDGVPSRFSGSRYGTDFTLTISSLED
EDLATYFCLQHSYLPYTFGGGTKLEIKR
(SEQ ID NO: 2)

As shown in Table 2, an amino acid sequence may contain various combinations of the bases, as represented by the one-letter abbreviations for the standard amino acids. The amino acid sequence shown in Table 2 recites amino acids selected from the 22 standard (proteinogenic or natural) amino acids, but sequences comprising nonstandard amino acid sequences may also be used.

FIG. 2 illustrates an index 200 of a nucleic acid sequence, consistent with embodiments disclosed herein. Although FIG. 2 illustrates use of nucleic acid sequences, one of ordinary skill in the art would understand how such an example would apply to other types of sequences, such as RNA sequences (e.g., involving the bases adenine, guanine, uracil, and cytosine), sequences of artificially synthesized polymers (such as PNA), and amino acid sequences, including standard (proteinogeneic or natural) and non-standard (non-proteinogenic or non-natural) amino acids.

As shown in FIG. 2, index 200 includes a plurality of elements corresponding to various permutations of nucleic acid sequences. In the case of FIG. 2, each permutation is 16 bases in length, resulting in an index with $4^{16}$ or 4,294,967,296 elements (note that each base of a nucleic acid sequence is one of four types). More generally, the size or the number of elements of index 200 is equal to $4^k$, where k is the length, in bases, of each permutation.

As shown to the left of each element in FIG. 2, a given element of the index may be referred to by its position number. For example, as illustrated in FIG. 2, position "0" refers to the element corresponding to the permutation "AAAAAAAAAAAAAAAA (SEQ ID NO: 3)" (which is also indicated by reference number 202a), position "3" refers to the element corresponding to the permutation "AAAAAAAAAAAAAATT (SEQ ID NO: 4)," and position "n" refers to the element corresponding to the permutation "GTAAGATCCGCTACAA (SEQ ID NO: 5)" (which is also indicated by reference number 202b). Because the index may have up to $4^k$ elements, as described above, the elements may be referenced beginning from position "0" to position "$4^k-1$."

In some embodiments, index 200 may contain a number of elements fewer than the number of possible permutations of sequences of a predetermined length. For instance, computer 101 may use statistical and/or probabilistic methods to reduce the number of elements so that only certain nucleic acid sequences (e.g., those most likely to occur) are included in the index. Such an index has the potential advantage of increased computational efficiency and reduction in memory requirements.

Continuing on, reference numbers 202a, 202b, 202c, and 202d of FIG. 2 represent different elements (e.g., elements "0," "n," "n+2," and "$4^k-1$," respectively) appearing in index 200. Reference numbers 204a, 204b, and 204c describe additional features of index 200. In particular, these reference numbers indicate position data storing certain elements of the index, i.e., reference numbers 204a and 204b indicate position data stored in element 202b, and reference number 204c indicates position data stored in element 202c. The index provides information about a nucleic acid sequence; thus, the position data stored in an element may reflect a position or location of the nucleic acid sequence in which the corresponding permutation occurs. For instance, as shown in FIG. 2, reference numbers 204a and 204b indicate that the permutation corresponding to element n of the index, "GTAAGATCCGCTACAA (SEQ ID NO: 5)," appears beginning at positions "0" and "21" of the nucleic acid sequence 206. Similarly, reference number 204c indicates that the permutation corresponding to element n+2 of the index, "GTAAGATCCGCTACTA (SEQ ID NO: 6)," appears beginning at position "44" of the nucleic acid sequence 206.

The nucleic acid elemental sequences may be received from an underlying nucleic acid sample sequence, which may be much greater in length (e.g., millions or billions of bases).

Figure 3:
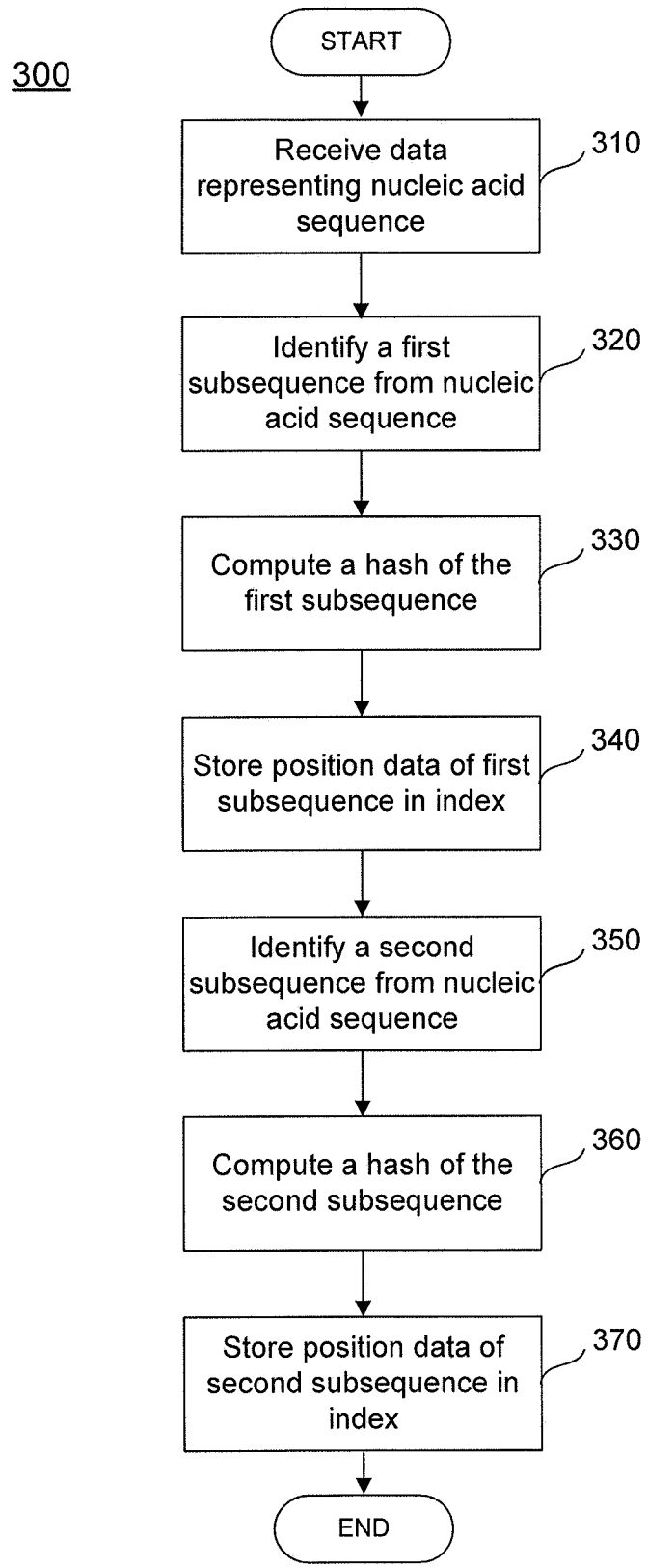
FIG. 3 is a flowchart illustrating an example method for creating an index of a digital input reflecting a nucleic acid sequence or an amino acid sequence, consistent with embodiments disclosed herein.

FIG. 3 is a flowchart illustrating a method 300 for creating an index of a digital input reflecting a nucleic acid sequence or an amino acid sequence, consistent with embodiments disclosed herein. Memory 106 may include a set of instructions—such as a program, software, or firmware—that, when executed by computer 101, can be used to implement the method illustrated in FIG. 3.

Method 300 begins at step 310, where computer 101 receives data representing a sequence, such as a nucleic acid sequence. The type and length of the sequence may vary and is not critical; for example, the sequence may be a nucleic acid sequence that is millions or billions of bases in length. The origin of the data representing the sequence may vary and is not critical; for example, the data may originate from computer 101 or it may be received by computer 101 from a second computer via network 108. At step 320, computer 101 identifies a first subsequence of the nucleic acid sequence from a first position of the nucleic acid sequence. The subsequence may be of varying length (e.g., 200 bases, 300 bases) and may be taken from various positions or locations of the nucleic acid sequence.

Continuing on to step 330, computer 101 computes a hash of the first subsequence. More specifically, computer 101 may determine an element of the index (such as index 200) corresponding to the first subsequence, based on the contents (e.g., the permutation of bases) of the first subsequence. As discussed above in connection with FIG. 2, the index may contain a plurality of elements, where each element corresponds to a permutation of a nucleic acid sequence. For example, an index containing elements that correspond to permutations 16 bases in length, where each base is one of 4 types of bases, may have $4^{16}$ or 4,294,967, 296 total elements. In computing the hash, computer 101 may implement a hashing algorithm that, for each element of the index, assigns a corresponding permutation. As illustrated in FIG. 2, for instance, element "0" corresponds to the permutation "AAAAAAAAAAAAAAAA (SEQ ID NO: 3)," and element "n" corresponds to the permutation "GTAAGATCCGCTACAA (SEQ ID NO: 5)." In some embodiments, computer 101 may implement a "no-collision hash," such that each element of the index corresponds to a unique permutation and no two elements correspond to the same permutation.

For instance, computer 101 may implement a no-collision hash algorithm that computes the hash of a given sequence (such as a nucleic acid sequence) by summing values assigned to each element (such as a base) of the sequence. More specifically, computer 101 may compute the hash of a nucleic acid sequence $e_1e_2 \ldots e_n$ according to the following equation: $\text{hash}(e_1e_2 \ldots e_n) = \text{val}(e_1)*4^0 + \text{val}(e_2)*4^1 + \ldots + \text{val}(e_n)*4^{n-1}$, where $\text{val}(e_i)$ is a numerical value assigned to each respective base. By way of illustration, if $\text{val}("A")=0$, $\text{val}("C")=1$, $\text{val}("G")=2$, and $\text{val}('T')=3$ (recall that A, C, G, and T are shorthand for the four types of bases in a nucleic acid sequence), then the hash of the sequence "AGTCCG" is computed as: $\text{hash}(\text{AGTCCG})=0*4^0+2*4^1+3*4^2+1*4^3+1*4^4+2*4^5=2424$.

At step 340, computer 101 stores position or location data of the first subsequence in the index. In some embodiments, computer 101 stores this data in an element of the index corresponding to the first subsequence, where the corresponding element is determined by computing a hash of the first subsequence, as described above in connection with step 330. Computer 101 may store this data using a variety of data structures, including but not limited to, databases, matrices, arrays, linked lists, trees, and the like. The choice of data structure(s) is not critical to any embodiment. As described above in connection with FIG. 2, the position data reflects a first position of the nucleic acid sequence in which the first subsequence occurs. Additionally, a given subsequence may appear more than once in the nucleic acid sequence. For example, as shown in FIG. 2, the subsequence "GTAAGATCCGCTACAA (SEQ ID NO. 5)" (reference number 202b) occurs at positions "0" and "21" of the nucleic acid sequence (reference numbers 204a and 204b, respectively). Thus, computer 101 may store position data in a given element of the index reflecting multiple positions of the nucleic acid sequence (e.g., in which the corresponding permutation appears).

At step 350, similar to the description of step 320, above, computer 101 retrieves a second subsequence of the nucleic acid sequence from a second position of the nucleic acid sequence. The content of the second subsequence may or may not be different from the first subsequence. In some embodiments, computer 101 may retrieve the second subsequence from the nucleic acid sequence based on the position from which computer 101 retrieved the first subsequence. For example, computer 101 may receive the second subsequence from a second position of the nucleic acid sequence that is offset from the first position of the nucleic acid sequence by a number of bases (e.g., 1 base).

At step 360, computer 101 computes a hash of the second subsequence. Computer 101 may perform step 360 in a manner similar to the description of step 330, above. Next, at step 370, computer 101 stores position or location data of the second subsequence into the index. Computer 101 may perform step 370 in a manner similar to the description of step 340, above. In addition, computer 101 may, in some cases, store the position data of the second subsequence in the element of the index in which computer 101 stored the position data of the first subsequence. This situation may occur, for example, when the first and second subsequences are identical.

Figure 4:
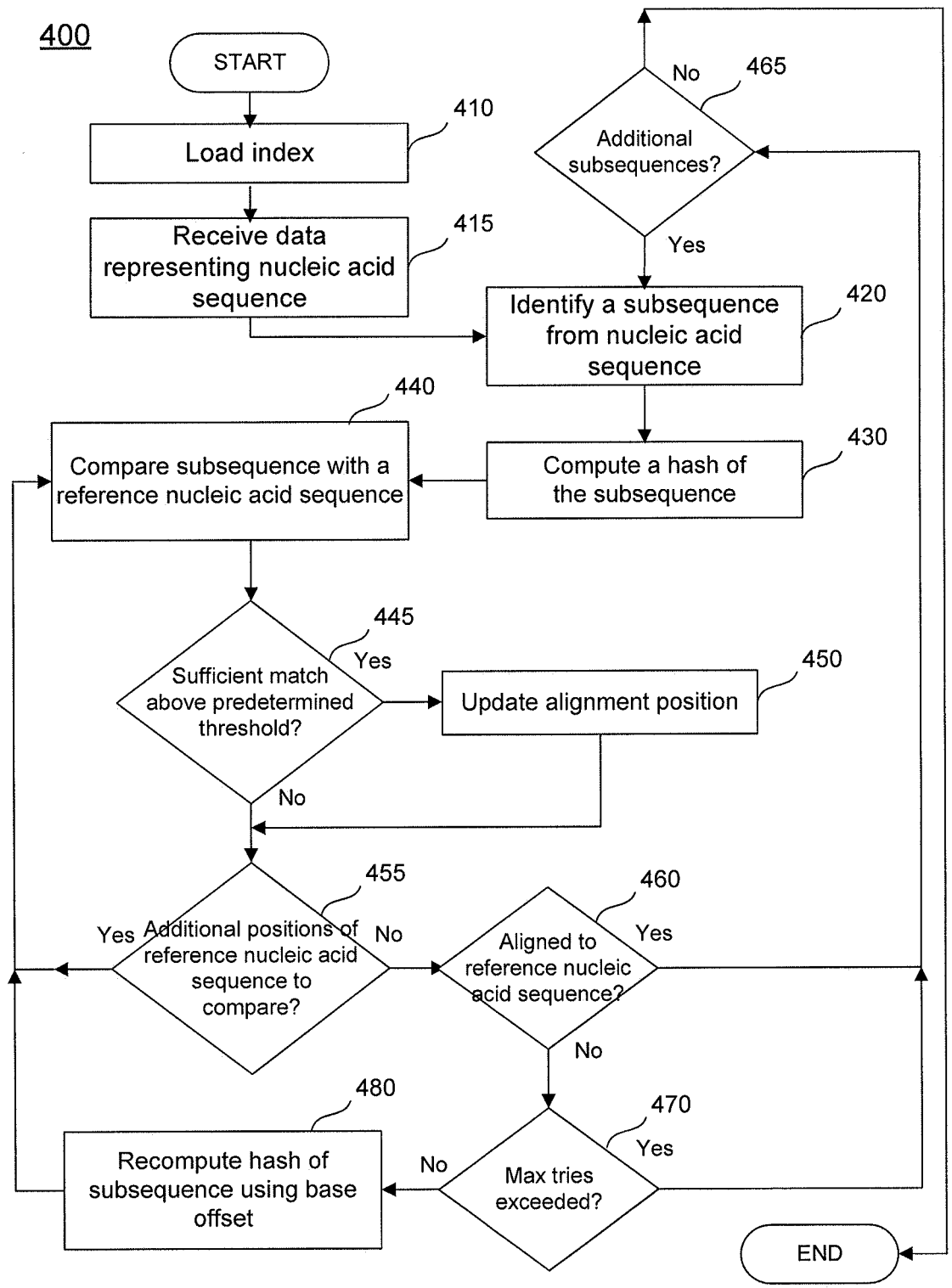
FIG. 4 is a flowchart illustrating an example method for aligning a digital input reflecting a nucleic acid sequence using an index of a reference nucleic acid sequence, consistent with embodiments disclosed herein.

FIG. 4 is a flowchart illustrating a method 400 for aligning data representing a nucleic acid sequence using an index of a reference nucleic acid sequence, consistent with embodiments disclosed herein. Method 400 begins at step 410, where computer 101 loads an index of a reference nucleic acid sequence. The index may have been generated, for example, by computer 101 using method 300, described in connection with FIG. 3 above. At step 415, computer 101 receives a digital input reflecting a nucleic acid sequence. The length of the nucleic acid sequence may vary and is not critical.

At step 420, computer 101 identifies a subsequence of the nucleic acid sequence from a first position of the nucleic acid sequence. The subsequence may be of varying length (e.g., 200 bases, 300 bases) and may be taken from various positions or locations of the nucleic acid sequence. In some embodiments, the subsequence may be referred to as a "read" of the nucleic acid sequence.

At step 430, similar to the description of step 330, above, computer 101 computes a hash of the subsequence. In some embodiments, computer 101 computes the hash based on a subset of bases listed in the subsequence. For example, the hash may be computed using the first 16 bases listed in the subsequence. More generally, computer 101 may compute the hash using a number of bases equal to the length k of each permutation of bases corresponding to elements of the index.

Continuing to step 440, computer 101 compares the subsequence with a reference nucleic acid sequence. The index provides information on the reference nucleic acid sequence, including the positions of the reference nucleic acid sequence in which different permutations of bases appear. Computer 101 may use the hash of the subsequence to determine the corresponding element of the index containing the position data representing where the permutation (e.g., of the corresponding element) appears in the reference nucleic acid sequence. Thus, at step 440, computer 101 may compare the subsequence with the reference nucleic acid sequence at the positions of the reference nucleic acid sequence indicated by the position data.

To illustrate, referring again to FIG. 2, computer 101 may compute the hash of the subsequence resulting in corresponding element n of the index. Element n, which corresponds to the permutation "GTAAGATCCGCTACAA (SEQ ID NO:5)," also includes position data "0" and "21," as indicated by reference numbers 204a and 204b, respectively. In other words, the permutation "GTAAGATCCGCTACAA (SEQ ID NO: 5)" appears beginning at positions "0" and "21" of the reference nucleic acid sequence. Thus, computer 101 may compare, base-by-base, the subsequence with the reference nucleic acid sequence beginning at position "0" and position "21." For example, the base in the 1st position of the subsequence may be compared with the base at position "21" of the reference nucleic acid sequence, and the base in the 2nd position of the subsequence may be compared with the base at position "22" of the reference nucleic acid sequence, and so on. More generally, the base in the first position of the subsequence is compared with the base in the first position of the reference nucleic acid sequence, the base in the second position of the subsequence is compared with the base in the second position of the reference nucleic acid sequence, and so on.

Continuing on to step 445, computer 101 checks whether the two sequences match above a predetermined threshold. For example, if the sequences match base-by-base except at two positions, computer 101 may determine that the sequences match. In some embodiments, computer 101 may terminate the comparison before all of the base-by-base comparisons have been performed, such as when the number of mismatches between the sequences exceeds a maximum number of permitted mismatches. This embodiment results in the advantage of increasing the efficiency of computer 101 by enabling it reduce processing times and reallocate resources to other processing-intensive tasks.

Next, if computer 101 determines that the two sequences match, computer 101 updates the alignment position at step 450. In some embodiments, the alignment position refers to the first position at which the subsequence matches the reference nucleic acid sequence. Furthermore, if the subsequence does not exactly match the reference nucleic acid sequence at any position, the alignment position may refer to the first position at which the subsequence best matches the reference nucleic acid sequence. Computer 101 may update the alignment position as additional comparisons are made between the subsequence and the reference nucleic acid sequence.

At step 455, computer 102 checks whether there are additional positions of the reference nucleic acid sequence to compare with the subsequence. If there are, computer 101 returns to step 440 and repeats the steps described above. Otherwise, continuing on to step 460, computer 101 checks whether the subsequence is aligned to the reference nucleic acid sequence. If there is alignment, computer 101 proceeds to step 465 to determine whether there are additional subsequences to process. Once all subsequences have been processed (e.g., as illustrated by the flow chart in FIG. 4), method 400 ends. If at least one subsequence has not been processed, computer 101 proceeds to step 420 and repeats the steps described above.

Returning back to step 460, if computer 101 determines that the subsequence is not aligned to the reference nucleic acid sequence, computer 101 recomputes the hash of the subsequence using a base offset, at step 480. Before doing so, however, computer 101 first checks at step 470 the number of times that it previously recomputed the hash for the subsequence. If this number exceeds a maximum permitted number (e.g., 3 tries), computer 101 instead proceeds to step 465 to determine whether there are additional subsequences to process. Returning to step 480, processing unit 102 may recompute the hash by, for example, using a different subset of bases in the subsequence to compute the hash. If at step 430 computer 101 computed the hash using the first 16 bases (e.g., the bases at positions 1-16 of the subsequence) of the subsequence, for instance, computer 101 may recompute the hash at step 480 using the next 16 bases (e.g., the bases at positions 17-32 of the subsequence). Upon recomputing the hash, computer 101 proceeds to step 440 and repeats the steps described above.

Figure 5:
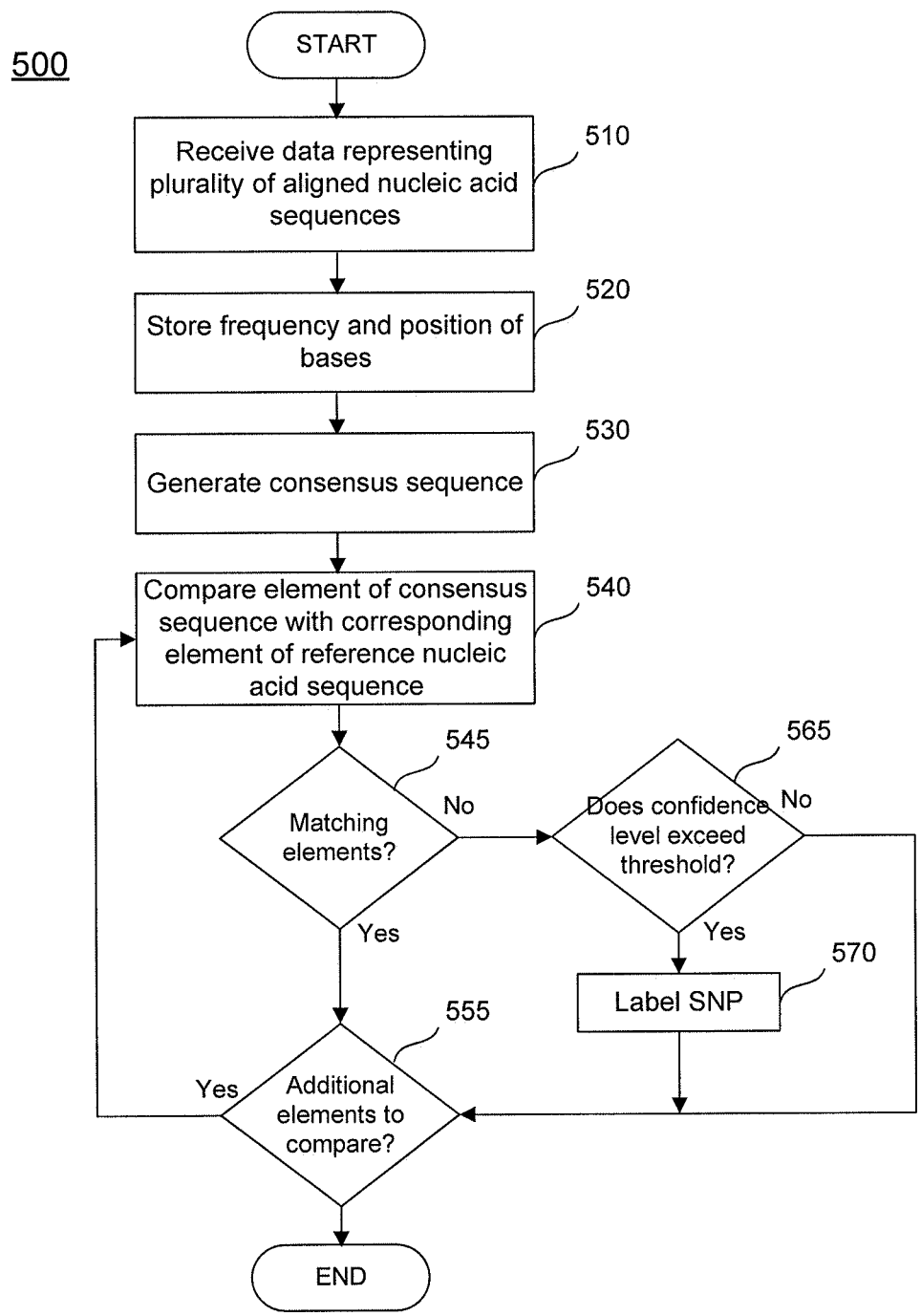
FIG. 5 is a flowchart illustrating an example method for detecting an SNP in a digital input reflecting a nucleic acid sequence, consistent with embodiments disclosed herein.

FIG. 5 is a flowchart illustrating a method 500 for detecting an SNP in a digital input reflecting a nucleic acid sequence, consistent with embodiments disclosed herein. Method 500 begins at step 510, where computer 101 receives data representing reflecting a plurality of aligned nucleic acid sequences. The length of the nucleic acid sequences may vary and is not critical. The plurality of nucleic acid sequences may have been aligned using the steps described in connection with method 400, above.

At step 520, computer 101 stores the frequency and positions of the bases listed in each of the aligned nucleic acid sequences. The data may be stored, for example, locally in memory 106 or on another computer accessed over network 108.

For instance, computer 101 may keep track of the number of times that each base (i.e., adenine, guanine, thymine, and cytosine) occurs, as well as the relative position of each occurrence, in each aligned nucleic acid sequence. The relative position may refer to the position at which the aligned nucleic acid sequence was aligned to the reference nucleic acid sequence, as described above, for example, in connection with FIG. 4.

To illustrate, an aligned nucleic acid sequence X, which may be 200 bases in length and is aligned with a reference nucleic acid sequence at position 772, may begin with the bases "ATT . . . ." Thus, computer 101 stores one occurrence of the base adenine at position 772, one occurrence of the base thymine at position 773, and one occurrence of the base thymine at position 774, and so forth.

In some embodiments, computer 101 may store the occurrences of each base in separate data structures. For example, computer 101 may use a separate array for each base (e.g., an array of integers or natural numbers), where the length of each array is set to the length of the reference nucleic acid sequence. Computer 101 would then increment the element of the respective array corresponding to the position and the base occurrence. Thus, after computer 101 stores the occurrences of each base in the aligned nucleic acid sequences, the array elements would indicate the total number of times that each base occurred in a given position. The choice and the use of data structures may vary and are not critical to any embodiment.

At step 530, computer 101 generates a consensus sequence. Computer 101 may set the length of the consensus sequence to be the same length as the reference nucleic acid sequence, and each element of the consensus sequence may correspond to a position of the reference nucleic acid sequence. As described above, computer 101 at step 520 records the occurrences of each base in the aligned nucleic acid sequences, in each position corresponding to the reference nucleic acid sequence. In some cases, more than one base type may have occurred in a given position, due to, for example, mutations or bad or corrupted sequences. Therefore, the elements of the consensus sequence may indicate the base type that most likely corresponds to each position of the reference nucleic acid sequence. Computer 101 at step 530 may determine the elements of the consensus sequence based on the base with the highest occurrence count. In some embodiments, computer 101 may compare a ratio of the base with the highest occurrence count over the total occurrences of all bases to a predetermined confidence threshold. If the ratio is less than the predetermined confidence threshold (e.g., 0.8 or 80 percent), then computer 101 may determine the corresponding element of the consensus sequence to be "no consensus," rather than the base type with the highest occurrence count.

Continuing on to step 540, computer 101 compares the generated consensus sequence with the reference nucleic acid sequence. Computer 101 may perform the comparison base-by-base, i.e., the first element of the consensus sequence may be compared with the first element of the reference nucleic acid sequence, the second element of the consensus sequence may be compared with the second element of the reference nucleic acid sequence, and so on.

At step 545, computer 101 checks whether two bases are the same or different. If the two bases are the same, the process proceeds to step 555, at which point computer 101 checks whether there are additional elements to compare between the consensus sequence and the reference nucleic acid sequence. If so, computer 101 returns to step 540 and repeats the steps described above.

Going back to step 545, if the two bases are different, computer 101 checks at step 565 whether the confidence level associated with the element of the consensus sequence exceeds a predetermined confidence level threshold. The confidence level may be determined in a manner similar to the ratio calculation described in connection with steps 520 and 530, above. The predetermined confidence level threshold may be the same or different as the predetermined confidence threshold described above. Turning back to step 565, if the confidence level exceeds a predetermined confidence level threshold, computer 101 determines at step 570 that the element of the consensus sequence is an SNP. Otherwise, the process proceeds directly to step 555, which has been described above. One of skill in the art would understand how the flowchart illustrated in FIG. 5 would apply to detecting differences in other sequences, such as substitutions in amino acid sequences.

Figure 6:
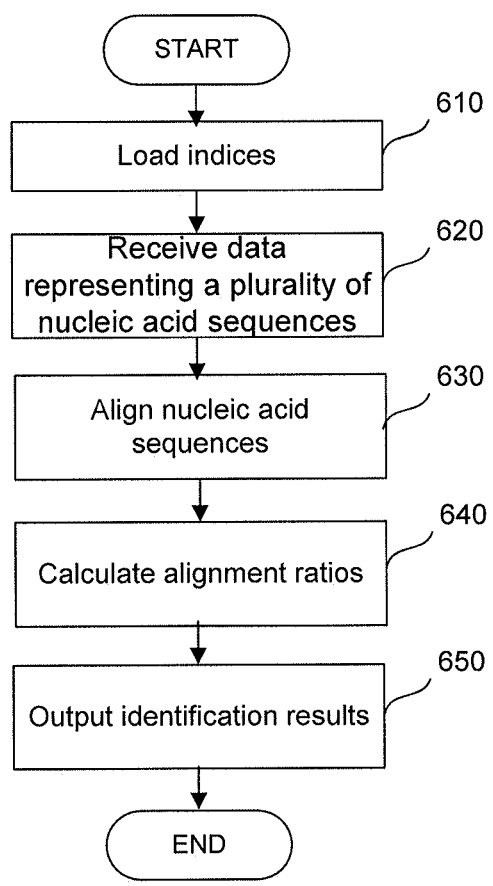
FIG. 6 is a flowchart illustrating an example method for identifying one or more species in a digital input reflecting a nucleic acid sequence using at least one index of at least one reference nucleic acid sequence, consistent with embodiments disclosed herein.

FIG. 6 is a flowchart illustrating an method 600 for identifying one or more species in data representing a nucleic acid sequence using at least one index of at least one reference nucleic acid sequence, consistent with embodiments disclosed herein. Method 600 begins at step 610, where computer 101 loads at least one index of at least one reference nucleic acid sequence. The index or indices may have been generated, for example, by computer 101 using method 300, described in connection with FIG. 3 above. Computer 101 may load one or more indices representing reference nucleic acid sequences of different species, e.g., human, elephant, zebra, and the like. In some embodiments, computer 101 may load one "master" index that represents reference nucleic acid sequences of the different species. For example, the position data (e.g., reference numbers 204a, 204b, and 204c of FIG. 2) included in elements of the index may be associated with a given species (or a plurality of species, in the case of overlap). The choice of implementation (e.g., an index or indices) representing reference nucleic acid sequences of different species may vary and is not critical to any embodiment.

At step 620, computer 101 receives a digital input reflecting a plurality of nucleic acid sequences. At step 630, computer 101 aligns the plurality of nucleic acid sequences to each of the reference nucleic acid sequences represented by the indices loaded at step 610. Computer 101 may perform the alignment using the methods described in connection with FIG. 4, above.

Continuing on to step 640, computer 101 calculates alignment ratios for the aligned nucleic acid sequences with respect to each of the reference nucleic acid sequences. For a given reference nucleic acid sequence, computer 101 may calculate the ratio by dividing the number of nucleic acid sequences aligned to the reference nucleic acid sequence by the total number of nucleic acid sequences loaded at step 620. To illustrate, consider the case where three indices representing reference nucleic acid sequences are used (e.g., human, elephant, zebra). If there are 100 nucleic acid sequences, 60 of the 100 may have aligned to the Human index, 30 of the 100 may have aligned to the elephant index, and 10 of the 100 may have aligned to the zebra index. In such a case, the respective alignment ratios would then be 0.60 (or 60 percent), 0.30 (or 30 percent), and 0.10 (or 10 percent).

Computer 101 outputs the calculated alignment ratios at step 650. In some embodiments, computer 101 may display the three highest calculated ratios and an identification of the associated reference nucleic acid sequences. Computer 101 may also display the calculated ratios that exceed a predetermined ratio threshold.

It is to be understood that, although the systems and processes disclosed herein have been described in the field of genomics, such indexing technology may have applications in other areas. For example, and by way of illustration only, the indexing technology may be useful in text mining applications (e.g., creating an index of thousands of texts that would enable matching of keywords) or knowledge management applications (e.g., creating an index of expert reports by subject matter, enabling the discovery of overlapping concepts and projects the matching of shared expertise).

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in, or by means of, Java, C, C++, assembly language, or any such programming languages. One or more of such software sections or modules can be integrated into a computer system, computer readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

The invention claimed is:

1. A system for identifying one or more species in an undifferentiated environmental sample comprising a plurality of nucleic acid sequences corresponding to one or more species, the system comprising:
   a processor; and
   a memory storing instructions executable by the processor to cause the system to:
      generate and store at least one generated index of the one or more indices;
      receive reference data representing a reference nucleic acid sequence associated with the generated index;
      identify, in the reference data, a first reference subsequence of the reference nucleic acid sequence associated with the generated index, wherein the first reference subsequence is retrieved from a first position of the nucleic acid sequence associated with the generated index;
      compute a hash of the first reference subsequence to determine a first corresponding element of the generated index; and
      store, in the first corresponding element of the generated index, position data reflecting the first position and indicating the reference nucleic acid sequence associated with the generated index;
      load one or more indices, including the at least one generated index, representing a plurality of reference nucleic acid sequences, wherein the one or more indices each comprises a respective plurality of elements, each element corresponding to a potential nucleic acid sequence permutation, wherein the one or more indices are limited, based on statistical methods regarding which permutations are most likely to occur, to less than a total possible number of permutations,
      receive data comprising a plurality of data structures, each of the plurality of data structures digitally representing a respective nucleic acid sequence;
      for each of the nucleic acid sequences in the received data, attempt to align the nucleic acid sequence to each of reference nucleic acid sequences using the one or more indices;
      for each of the nucleic acid sequences in the received data, determine, using the one or more indices, whether the nucleic acid sequence is successfully aligned to any one or more of the reference nucleic acid sequences;
      for each one of the reference nucleic acid sequences, calculate a respective alignment ratio based on the number of nucleic acid sequences that were determined to be successfully aligned to the respective reference nucleic acid sequence and based on the total number of nucleic acid sequences in the received data; and
      generate and store the plurality of calculated alignment ratios for the received data.

2. The system of claim 1, wherein attempting to align a nucleic acid sequence to each of reference nucleic acid sequences and determining whether a nucleic acid sequence is successfully aligned to any one or more of the reference nucleic acid sequences comprises, for a given nucleic acid sequence in the received data and a given reference nucleic acid sequence:

identifying, in a the portion of the received data associated with the given nucleic acid sequence, a subsequence of the given nucleic acid sequence;

computing a hash of the subsequence to determine a corresponding element of the one or more indices, wherein the corresponding element includes position data reflecting one or more positions of the given reference nucleic acid sequence containing a part of the subsequence;

comparing the subsequence with the given reference nucleic acid sequence at the one or more positions of the given reference nucleic acid sequence;

determining, based on the comparison, whether a number of bases greater than a predetermined threshold number of bases are mismatched; and determining, when the number of mismatched bases is less than the predetermined threshold number of bases, that the subsequence is aligned with the given reference nucleic acid sequence.

3. The system of claim 1, wherein the instructions are executable by the processor to cause the system to display one or more of the highest alignment ratios of the plurality of calculated alignment ratios.

4. The system of claim 1, wherein the instructions are executable by the processor to cause the system to display an alignment ratio of the plurality of calculated alignment ratios in accordance with a determination that the alignment ratio exceeds a predetermined ratio threshold.

5. The system of claim 1, wherein the one or more indices comprise a single index representing the plurality of reference nucleic acid sequences.

6. The system of claim 1, wherein the one or more indices comprises a plurality of species-specific indices, each species-specific index of the plurality of species-specific indices representing a reference nucleic acid sequence of a single specific species.

7. The system of claim 1, wherein the instructions are executable by the processor to cause the system to:

generate and store at least one generated index of the one or more indices;

receive reference data representing a reference nucleic acid sequence associated with the generated index;

identify, in the reference data, a first reference subsequence of the reference nucleic acid sequence associated with the generated index, wherein the first reference subsequence is retrieved from a first position of the nucleic acid sequence associated with the generated index;

compute a hash of the first reference subsequence to determine a first corresponding element of the generated index; and store, in the first corresponding element of the generated index, position data reflecting the first position and indicating the reference nucleic acid sequence associated with the generated index.

8. The system of claim 7, wherein the instructions are executable by the processor to cause the system to:

identify, in the reference data, a second reference subsequence of the nucleic acid sequence associated with the generated index, wherein the second reference subsequence is retrieved from a second position of the nucleic acid sequence associated with the generated index different from the first position;

compute a second hash of the second reference subsequence to determine a second corresponding element of the generated index; and store, in the second corresponding element of the generated index, position data reflecting the second position and indicating the reference nucleic acid sequence associated with the generated index.

9. The system of claim 8, wherein the second position is offset from the first position by one base.

10. The system of claim 1, wherein the nucleic acid sequence comprises one of DNA, cDNA, RNA, mRNA, or PNA.

11. The system of claim 1, wherein the length of the subsequence is 16 bases.

12. A non-transitory computer-readable storage medium for identifying one or more species in an undifferentiated environmental sample comprising a plurality of nucleic acid sequences corresponding to one or more species, the non-transitory computer-readable storage medium storing instructions configured to be executed by a system comprising a processor to cause the system to:

generate and store at least one generated index of the one or more indices;

receive reference data representing a reference nucleic acid sequence associated with the generated index;

identify, in the reference data, a first reference subsequence of the reference nucleic acid sequence associated with the generated index, wherein the first reference subsequence is retrieved from a first position of the nucleic acid sequence associated with the generated index;

compute a hash of the first reference subsequence to determine a first corresponding element of the generated index; and store, in the first corresponding element of the generated index, position data reflecting the first position and indicating the reference nucleic acid sequence associated with the generated index;

load one or more indices, including the at least one generated index, representing a plurality of reference nucleic acid sequences, wherein the one or more indices each comprises a respective plurality of elements, each element corresponding to a potential nucleic acid sequence permutation, wherein the one or more indices are limited, based on statistical methods regarding which permutations are most likely to occur, to less than a total possible number of permutations, receive data comprising a plurality of data structures, each of the plurality of data structures digitally representing a respective nucleic acid sequence;

for each of the nucleic acid sequences in the received data, attempt to align the nucleic acid sequence to each of reference nucleic acid sequences using the one or more indices;

for each of the nucleic acid sequences in the received data, determine, using the one or more indices, whether the nucleic acid sequence is successfully aligned to any one or more of the reference nucleic acid sequences;

for each one of the reference nucleic acid sequences, calculate a respective alignment ratio based on the number of nucleic acid sequences that were determined to be successfully aligned to the respective reference nucleic acid sequence and based on the total number of nucleic acid sequences in the received data; and generate and store the plurality of calculated alignment ratios for the received data.

13. A method for identifying one or more species in an undifferentiated environmental sample comprising a plurality of nucleic acid sequences corresponding to one or more species, the method performed at a system comprising a processor and memory, the method comprising:
  generating and storing at least one generated index of the one or more indices;
  receiving reference data representing a reference nucleic acid sequence associated with the generated index;
  identifying, in the reference data, a first reference subsequence of the reference nucleic acid sequence associated with the generated index, wherein the first reference subsequence is retrieved from a first position of the nucleic acid sequence associated with the generated index;
  computing a hash of the first reference subsequence to determine a first corresponding element of the generated index; and
  storing, in the first corresponding element of the generated index, position data reflecting the first position and indicating the reference nucleic acid sequence associated with the generated index;
  loading one or more indices, including the at least one generated index, representing a plurality of reference nucleic acid sequences, wherein the one or more indices each comprises a respective plurality of elements, each element corresponding to a potential nucleic acid sequence permutation, wherein the one or more indices are limited, based on statistical methods regarding which permutations are most likely to occur, to less than a total possible number of permutations,
  receiving data comprising a plurality of data structures, each of the plurality of data structures digitally representing a respective nucleic acid sequence;
  for each of the nucleic acid sequences in the received data, attempting to align the nucleic acid sequence to each of reference nucleic acid sequences using the one or more indices;
  for each of the nucleic acid sequences in the received data, determining, using the one or more indices, whether the nucleic acid sequence is successfully aligned to any one or more of the reference nucleic acid sequences;
  for each one of the reference nucleic acid sequences, calculating a respective alignment ratio based on the number of nucleic acid sequences that were determined to be successfully aligned to the respective reference nucleic acid sequence and based on the total number of nucleic acid sequences in the received data; and
  generating and storing the plurality of calculated alignment ratios for the received data.

* * * * *